United States Patent
Hovorka

[11] Patent Number: 6,060,321
[45] Date of Patent: *May 9, 2000

[54] SUN TAN DOSIMETER

[76] Inventor: George B. Hovorka, Idolon Technology 72 Stone Pl., Melrose, Mass. 02176

[ * ] Notice: This patent issued on a continued prosecution application filed under 37 CFR 1.53(d), and is subject to the twenty year patent term provisions of 35 U.S.C. 154(a)(2).

[21] Appl. No.: 09/110,777

[22] Filed: Jul. 6, 1998

Related U.S. Application Data

[60] Provisional application No. 60/057,012, Jul. 11, 1997.

[51] Int. Cl.$^7$ .................................................. G01N 31/22
[52] U.S. Cl. ............................... 436/57; 422/56; 422/57; 422/58; 436/58; 436/166
[58] Field of Search .................... 422/56–58, 61; 436/57, 58, 166

[56] References Cited

U.S. PATENT DOCUMENTS

| | | | |
|---|---|---|---|
| 1,262,444 | 5/1918 | Capstaff . | |
| 2,046,409 | 7/1936 | Plishke | 95/10 |
| 2,083,675 | 6/1937 | Ville | 95/8 |
| 2,949,880 | 8/1960 | Fromer | 116/114 |
| 3,051,837 | 8/1962 | Nitka | 250/83 |
| 3,194,963 | 7/1965 | McKee | 250/6 |
| 3,710,115 | 1/1973 | Jubb | 250/83.3 |
| 3,742,240 | 6/1973 | Jonasson | 250/372 |
| 3,787,687 | 1/1974 | Trumble | 250/83 |
| 3,903,423 | 9/1975 | Zweig | 250/474 |
| 3,917,948 | 11/1975 | Strutz | 250/372 |
| 4,010,372 | 3/1977 | Strutz | 250/372 |
| 4,065,672 | 12/1977 | Harpst | 250/373 |
| 4,308,459 | 12/1981 | Williams | 250/474 |
| 4,372,680 | 2/1983 | Adams et al. | 356/511 |
| 4,389,217 | 6/1983 | Baughman | 436/21 |
| 4,428,050 | 1/1984 | Pellegrino | 364/414 |
| 4,704,535 | 11/1987 | Leber | 250/372 |
| 4,788,433 | 11/1988 | Wright | 250/474.1 |
| 4,818,491 | 4/1989 | Fariss | 422/56 |
| 4,882,598 | 11/1989 | Wulf | 250/338 |
| 4,962,910 | 10/1990 | Shimizu | 250/372 |
| 5,008,548 | 4/1991 | Gat | 250/372 |
| 5,075,557 | 12/1991 | Harasawa | 250/474.1 |
| 5,192,639 | 3/1993 | Hirai | 430/138 |
| 5,382,968 | 1/1995 | Endoh | 346/153.1 |
| 5,436,115 | 7/1995 | Mullis | 430/388 |
| 5,500,532 | 3/1996 | Kozicki | 250/372 |
| 5,589,398 | 12/1996 | Krause | 436/164 |

FOREIGN PATENT DOCUMENTS

| | | |
|---|---|---|
| 0 562 201 A1 | 9/1993 | European Pat. Off. . |
| 471 366 | 9/1937 | United Kingdom . |

OTHER PUBLICATIONS

Feigle in "Spot Tests in Organic Analysis", 7th Edition, 1966, pp. 130 through 131.

P.B. Issopoulos, Pharm. Acta Helv.64, Nr.3(1989), p. 82, second paragraph.

Krebs, V.B., entitled "Die Kristallstrutur von Mo03.2H20". Acta Cryst (1972) B28, 2222, pp. 2222–2231.

Boschen et al., entitled "Kristallstruktur den weissen Molybdansure", Acta Cryst. (1974) B330, 1795, pp. 1795–1800.

Sjobom et al., "Multicomponent Polyanions", Acta Chem. Scand. 27(1973) No. 10, pp. 3673–3691.

Day et al, "Synthesis and Characterization of the Dimolybdate Ion", J, of Am. Chem. Soc. 99:18; Aug. 31, 1997 pp. 6147–6148.

*Primary Examiner*—Jill Warden
*Attorney, Agent, or Firm*—Pearson & Pearson

[57] ABSTRACT

A disposable ultraviolet dosimeter for rapid visual estimation of cumulative exposure to UV-A and UV-B radiation.

13 Claims, 1 Drawing Sheet

SUN TAN DOSIMETER

CROSS REFERENCES TO RELATED APPLICATIONS

This invention is related and complimentary to the invention of my provisional application, Ser. No. 60/057,012, filed Jul. 11, 1997.

BACKGROUND

1. Field of Invention

This invention relates generally to the monitoring of ultraviolet light, and more particularly to a device for monitoring cumulative exposure to ultraviolet light.

2. Description of Prior Art

Sunburn is a common illness, especially in the summer time, yet dangerous or even fatal, condition. Because of the popularity of sun tanning, consumers are continually exposed to the risk of sun burn. Therefore there is a need for a device that allows the consumer to easily determine the amount of cumulative ultraviolet (UV) exposure. This would enable the consumer to strike the balance between acquiring enough sun exposure to develop a tan yet avoid overexposure that leads to sunburn and other related medical problems.

Approximately five percent of the sunlight reaching the earth's surface is composed of ultraviolet radiation (200–400 nm). The near ultraviolet spectrum can be divided into three sub-regions: ultraviolet A (320–380 nm), ultraviolet B (280–320 nm) and ultraviolet C (200–280 nm). UV radiation has both positive and negative effects on the human body that may be felt either immediately or only decades after the occurrence or irradiation. The UV B (290–320 nm) region is responsible for most of the related biological effects.

The biological effects of UV light primarily effect the skin, eyes and immune system. Early damage includes dermatitis, conjunctivitis and keratitis. Delayed damage may include premature skin aging, skin cancer, exacerbation of skin diseases, cataracts, weakening of the immune system and skin cancer.

Sun tanning, especially if there is overexposure, can lead to many of the health consequences described above. The strength of sunlight is influenced by various factors including the seasons of the year, hour of the day, and geographical conditions.

The quantity of UV peaks between 11 AM and 2 PM. Because UV rays reach the earth's surface even on overcast days, it is difficult to estimate the quantity of UV from the brightness of the day. Therefore, cloudy weather represents a relatively high risk of sunburn because the warning effect of high temperature is missing. For those who desire sun exposure to obtain skin tanning for cosmetic purposes a more accurate method is needed to regulate the amount of exposure other than simple guessing. Of prime importance is that such sensing means be responsive to UV B radiation.

Chemical means have long been understood to be a method to measure sunlight and light exposure in general. An early example is the invention by Plishker U.S. Pat. No. 2,046,409, Jul. 7, 1936 that teaches a pocket sized light meter based on chemical means. This invention utilizes a housing in which contains a light sensing element. This said sensing element is exposed through a window in said housing during the period of light or sun exposure. The method disclosed in U.S. Pat. No. 2,949,880, Fromer, Aug. 23, 1960 teaches a sun tan control device based on a similar method. Both of these embodiments suffer from the necessity of complex housings and movable parts in order to utilize the invention. Chemical dip-sticks have also been developed to measure sun intensity. Such a method is disclosed in U.S. Pat. No. 5,589,398, Krause, Dec. 31, 1996. Such dip-sticks also suffer from the need of a housing or holder to properly position the dip-stick.

There are also a number of ultraviolet dosimeters based on label technology. This much more closely meets the needs of the consumer in so far that it can be worn while at the beach or performing other activities that involve exposure to the sun. Three of these devices utilize multi-layer polymeric label structures to measure the total dose of ultraviolet radiation and involve color change in response to increasing time in the sun.

There is the system of Zweig, U.S. Pat. No. 3,903,423, Sep. 2, 1975 that utilized a three or four layer label with a plastic film top layer with printed color scale. A similar multi-layer device is utilized by Trumble in U.S. Pat. No. 3,787,687, July 1974. Yet another multi-layer device is utilized by Wright in U.S. Pat. No. 4,788,433, November 1988. The methods disclosed by Zweig, Trumble and Wright, however, are relatively expensive to produce due to the requirement for a multi-layer polymeric system to house and support the photochromic material. Additionally, neither of these chemistry systems produce a color change that has the desirable tan coloration.

There is also the invention by Mullis, U.S. Pat. No. 5,436,115, Jul. 25, 1995 that discloses an ultraviolet sun sensor based on pH changes in a hydrogel. In commercial practice this invention suffers from the need to precisely control the amount of water in the hydrogel in order to get a pH change that is directly proportional to the amount of sun light exposure. In order to solve this limitation the commercial reduction of practice of the Mullis art involves a complex multi-layer polymeric system similar to Zweig, Trumble and Wright. Despite this increased complexity, this embodiment is still subject to shelf-life issues apparently due to the hydrogel drying out in the product over time. I have found that the relatively commercially unattractive characteristic of the prior art ultraviolet sun dosimeters may be overcome by incorporating a photochromic material that is active in the solid state directly into a printable emulsion. I have unexpectedly and surprisingly found that by incorporating ammonium dimolybdate into a vinyl acetate or poly(vinyl)alcohol emulsion, a label based dosimeter is created. Further, I have discovered that this emulsion can be screen printed with conventional techniques.

OBJECTS AND ADVANTAGES

Accordingly, several objects and advantages of my invention are to present a printable light sensitive pigment that will change in color over time. It is a further object of the instant invention to present a label based light dosimeter that is low cost and easy to manufacture with conventional screen printing equipment. It is still a further object of the instant invention to present a label based light dosimeter that develops a brown sun tan color over time when exposed to the sun. These and further objects of the instant invention will become more apparent to one skilled in the art upon reading the more detailed description set forth herein below:

Figure 1:
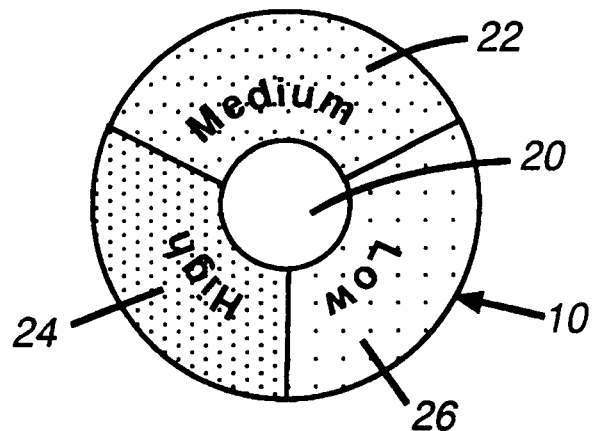
FIG. 1 is a perspective view of the sun tan dosimeter label.

Reference Numerals 10 ultraviolet light monitoring device
12 flat base member
14 color comparison panels
18 self stick adhesive
20 ultraviolet light sensing emulsion material
22 "medium" color standard comparison panel
24 "high" color standard comparison panel
26 "low" color standard comparison panel

SUMMARY

The present invention provides an improved device for monitoring the cumulative total amount of ultraviolet light exposure.

The ultraviolet radiation dosimeter of the present invention indicates the relative amount of accumulated ultraviolet light is inexpensively manufactured with conventional printing equipment.

It is a further object to provide a device that requires little skill to use, while providing direct quantification of the relative accumulated ultraviolet exposure.

It is a further object to optionally contain a color standard chart in close visual proximity to the color change area. The dosimeter can also contain means, such as a self-stick adhesive layer, to affix the dosimeter to the user.

The color change of this device which darkens from an initial white color to green to deepening shades of brown proportional to the cumulative amount of exposure to ultraviolet radiation. Thus, the device of this invention provides an indication of ultraviolet light exposure to help the user know when an accumulated amount of ultraviolet light in a given period of time has reached a level sufficient for tanning, yet safe from burning.

PREFERRED EMBODIMENT—DESCRIPTION

Figure 2:
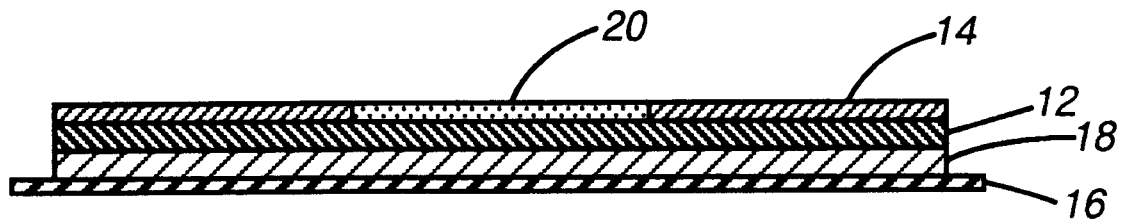
FIG. 2 shows a cross sectional view of the sun tan dosimeter label.

More specifically, the novel features of this sun tan dosimeter will become apparent from the following detailed description taken in conjunction with the accompanying drawings. Referring now to FIGS. 1 and 2 of the drawings, there is shown an ultraviolet light monitoring device 10, which is constructed in according to the invention. The device 10 is preferably a thin label patch and is adapted to be worn by the user during exposure to sun light. The device 10 includes a generally thin, flat base member 12 having color comparison panels 14 and is preferably coated with a self stick adhesive 18. The flat base member 12 is white in color and preferably 60 pound paper label stock. As will become apparent to those skilled in the art, other suitable label stocks may also be employed. A photosenitive test zone containing an ultraviolet light sensing emulsion material 20 is disposed on the face of the material in the form of a pattern or other graphics. Those substances are preferably used for the present invention which change their color upon exposure to sunlight. Such substances are known as chromogenic, whereby a color change is understood to be a change from one color to another or a color from a previously colorless substance. Within the scope of the invention those substances have proven to be particularly suitable which selectively absorb UV-B and UV-A radiation. In this sense ammonium dimolybdate (Aldrich Chemical Company, Milwaukee, Wis.) is excellently suited as the photoactive chromogenic substance that changes its color depending on the sunlight intensity and exposure period from white to brown. According to the invention the photoactive chromogenic substance can be mixed into a vinyl acetate emulsion such as Rovace 117 manufactured by Rohm Haas, Philadelphia, Pa. Other emulsions such as Elmer's Glue-All, manufactured by Elmer's Products, Inc. Columbus, Ohio or Weldbond Universal Space Age Adhesive, manufactured by Frank T. Ross & Sons LTD. Spring Grove, Ill., may be utilized. Color standard comparison panels 14 are placed adjacent to the ultraviolet sensing emulsion 20 for visible comparision by the user. The color standard comparison panels 14 can be printed with conventional printing means and inks that match the same visual appearance as the ultraviolet sensing emulsion. By providing the same appearance as the dye in the ultraviolet sensing emulsion, only the depth of color is to be considered as all other visual characteristics of the color standard panel and the ultraviolet sensing emulsion are identical. By keeping the reflectance and all other characteristics the same, even an unskilled and untrained eye can rapidly evaluate which color panel standard comes closest to matching the ultraviolet sensing emulsion with minimal interpolation. As a result, a useful reading of the cumulative exposure to ultraviolet light is obtained.

PREFERRED EMBODIMENT—OPERATION

Molecules that undergo both reversible and ir-reversible photo-induced color changes are termed photochromic systems. That is, in the absence of activating radiation, the system has a single stable electronic configuration. When the system is contacted with ultraviolet irradiation the absorption spectrum of the system undergoes a drastic change. The fundamental photo-electronic mechanism generally considered to produce photochromism is electronic delocalization. In inorganic crystals, photoiniated electron delocalization can lead to a colored state in which the electron is either trapped by a crystal defect to form a color center or otherwise reacts with the crystal host to leave the system in a colored state.

There are two major factors that govern the behavior of a photochromic system. First according the quantum theory, each absorbed quantum creates one activated molecule and only absorbed radiation can produce a chemical change. Variables which control the number of photons absorbed include: 1) The concentration and extinction coefficient of the photochrome. 2) The screening coefficients of other components of the system and 3) The wavelengths of the incident radiation. Second, all excited molecules will not undergo transformation to the colored form, so that the quantum yield will generally less than unity. Various deactivating processes include fluorescence, phosphorescence, and thermal release.

Although not wishing to be bound by any particular theory, it is possible that the photochromic phenomena of this dosimeter can be explained as follows. Since the photochromic color in this compound in an vinyl acetate or poly(vinyl)alcohol emulsion is a deep tan, the most likely theoretical alternative as to the nature of this photochromic reaction is that net electron delocalization to molybdenum take place either by an inter- or intra-phase photinitated electron transfer from the photo active material to the host emulsion.

The following examples illustrate the production of labels that undergo visible color changes upon exposure to near ultraviolet radiation. These labels will undergo this color change to an extent directly proportional to the cumulative amount of ultraviolet light incident upon the labels.

More specifically, Examples 1–2 illustrate the preparation of screen printed emulsions. Further, example 1 relates to the preparation of a label that utilizes such ultraviolet sensitive emulsion material. The examples which follow are for illustrative purposes only and are not intended in any way to limit the scope of the Applicant's invention.

Other aspects and advantage of the present invention will be apparent upon consideration of the following representative examples.

OTHER EMBODIMENTS

EXAMPLE 1

All parts and percentages are by weights unless otherwise specified. To an aqueous solution containing 30% Mowiol 40–88 (Hoechst) poly(vinyl)alcohol a concentration of ammonium dimolydbate, preferably 100 milligrams per ml of emulsion is mixed utilizing conventional techniques. Sheets of 60 lb label stock coated were with this mixture, preferably at one mil thickness, were found to develop a tan color when exposed to intense mid-day sunlight. As shown in FIG. 1, a portion of the label stock was cut into a circle about one half inch in diameter and placed at test zone 20 on flat base member 12 having on its surface three color standard panels. Panel 26, "low", matched the color of the test zone in ten minutes on a clear mid-june day in Melrose, Mass.; Panel 22 "medium", matched the test zone color obtained in 20 minutes; Panel 24, "high", matched the color obtained after 50 minutes. These rates of color conversion approximately agree with the UV index for that day and constitutes the range of time and individual should be exposed to intense sun light depending upon their skin pigmentation. If other rates of conversion are desired, the color change rate from an initial white color to green to sun tan brown can be adjusted by adding ultraviolet blocking agents such as Benzophenone (Aldrich Chemical Company, Milwaukee, Wis.), 4,4'-Isopropylidenebis(2,6-dichlorophenol) (Aldrich Chemical Company, Milwaukee, Wis.), Titanium(IV)oxide, -325 mesh (Aldrich Chemical Company, Milwaukee, Wis.) to the mixture.

The ultraviolet sensing emulsion material 20, can be coated onto the flat base member 12 with a conventional printing method such as silk screen printing. A #125 mesh polyester screen is preferred. In addition to the light sensing emulsion material 20, additional color standard comparison panels 22, 24 and 26 are placed adjacent to the ultraviolet sensing emulsion 20 for visible comparison by the user. The color standard can be printed with conventional printing means and inks that match the visual appearance of the ultraviolet sensing emulsion. These colors are stable in respect to ultraviolet exposure, and can be applied with conventional printing means such as lithographic, letter press, flexo, pad printing or screen printing. The device 10 is fabricated in sheets which are die cut into conveniently sized patches such as the illustrated one-inch round circle. Prior to die cutting, a self-stick adhesive 18 covered by a silicone peel-off backing strip 16, is affixed by suitable conventional techniques to a rear surface of the flat base member 12. The resulting one-inch round patches are thus easily attached to the user's skin or clothing in a position exposed to the sun by peeling off the backing strip 16 and pressing the adhesive 18 against a desired support surface. When the ultraviolet light sensing material 20, on the surface of the flat base member 12, develops full coloration to indicate the maximum recommended accumulated total exposure, the device 10 may be discarded or saved for a historical record and a new one employed.

EXAMPLE 2

This example demonstrates the color change with a similar molybdenum compounds. An emulsion was prepared as in Example 1, except ammonium heptamolydbate (Aldrich Chemical Company, Milwaukee, Wis.) was substituted for ammonium dimolydbate. The sensitivity to ultraviolet radiation and resultant color change were similar to Example 1. An emulsion was prepared as in Example 1 except potassium molydbate (Aldrich Chemical Company, Milwaukee, Wis.) was substituted for ammonium dimolydbate. The sensitivity to ultraviolet radiation was similar, but the resultant color change was weaker. An emulsion was prepared as in Example 1 except lithium molybdate (Aldrich Chemical Company, Milwaukee, Wis.) was substituted for ammonium dimolydbate. The sensitivity to ultraviolet radiation and resultant color change were similar to Example 1 but the resultant color had a green tint.

CONCLUSIONS, RAMIFICATIONS, AND SCOPE

It can be seen that the illustrated embodiment employs a round configuration, it is within the inventive concepts herein disclosed to employ various other shapes and arrangements. For example, the emulsion material 20 can be silk-screened in the shape of cartoon characters for use by children. The emulsion may be processed into other forms for attachment onto seals, emblems, rings, bracelets, timepieces, necklaces, pendants, brooches, buttons, tapes, headbands, sun visors, sunglasses, hats and caps, hair ornaments, belts, toys, mascots, ornaments, parasols, glove compartments, bags, towels, and the like. The solid support to which the emulsion is attached is not particularly limited to a round configuration and can be any one of various shapes such as ellipses, polygons, quadrilaterals, triangles, symbol shapes, letter shapes and patterns. Further, the light sensitive face may not be limited to a planar surface but may have a cubic structure of the sphere, hemisphere, cone, pyramid, concave-shape or the like.

This invention can also be used in marine biology or horticulture studies where the relationship between radiation exposure and life growth are required, since the invention can be mounted on a stem or other convenient structure.

This invention can also be used in the printing or semiconductor industry where it is important to routinely measure the output of ultraviolet radiation lamps used to cure ink and manufacture integrated circuits, since the invention can be mounted on a printing web or other convenient structure.

Since certain changes may be made in the above products without departing from the scope of the invention herein involved, it is intended that all matter contained in the above description, or shown in the accompanying drawings, shall be interpreted as illustrative and not in a limiting sense.

Thus the scope of the invention should be determined by the appended claims and their legal equivalents, rather than by the examples given.

What is claimed is:

1. A disposable, continuous reading, integrating, ultraviolet dosimeter for giving rapid visual estimation of the cumulative exposure to UV-A and UV-B radiation comprises a photosensitive test zone, wherein said test zone contains an emulsion dispersed therein ammonium dimolybdate, ammonium heptamolybdate, potassium molybdate or lithium molybdate, and adjacent thereto, at least one color standard panel which is a color intensity developed by the test zone is compared with the color of the color standard panel.

2. The dosimeter of claim 1 in which the photosensitive test zone contains UV blockers to control the rate of color development.

3. The dosimeter of claim 1 in which the color standard panel has at least three areas having colors corresponding to low, moderate and high levels of ultraviolet radiation exposure.

4. A process for preparation of a UV dosimeter for detecting UV-A and UV-B radiation suitable for visual evaluation characterized by a quantity of ammonium dimolybdate, ammonium heptamolybdate, potassium molybdate or lithium molybdate dispersed in an emulsion, and the UV light sensitive emulsion obtained applied on a carrier, preferably on a paper label stock by printing.

5. The process according to claim 4 characterized by the use of vinyl acetate as an emulsion.

6. The process according to claim 4 characterized by the use of poly(vinyl)alcohol as an emulsion.

7. The process according to claim 4 characterized by the use of UV blockers in the emulsion to control the rate of color change.

8. The process according to claim 4 characterized by the use of screen printing as the printing means.

9. A method for providing a direct visual estimation of the cumulative exposure to UV-A and UV-B radiation comprising the steps of:

attaching a patch to an area for detection of said radiation at said area;

providing in the center of said patch a test zone comprising an ultraviolet light sensing emulsion material which changes color when exposed to said UV-A and UV-B radiating, said emulsion material comprises a quantity of ammonium demolybdate, ammonium heptamolybdate, potassium molybdate or lithium molybdate dispersed therein; and surrounding said test zone with color panels to indicate detection of various amounts of said radiation when said color of said test zone matches one of said colored panels.

10. The method as recited in claim 9 wherein said step of surrounding said test zone with said color panels comprises the step of indicating a low amount of radiation by a white color panel, indicating a medium amount of radiation by a green color panel, and indicating a high amount of radiation by a brown color panel.

11. The method as recited in claim 9 wherein said step of providing a test zone comprises the step of providing UV blockers in said test zone to control the rate of color development.

12. The method as recited in claim 9 wherein said step of providing a test zone comprising an emulsion material comprises the step of providing vinyl acetate as said emulsion.

13. The method as recited in claim 9 wherein said step of providing a test zone comprising an emulsion material comprises the step of providing poly(vinyl)alcohol as said emulsion.

* * * * *